United States Patent
Elias

(10) Patent No.: US 11,484,523 B1
(45) Date of Patent: Nov. 1, 2022

(54) COMPOSITIONS FOR PREVENTION AND TREATMENT OF SYMPTOMS ASSOCIATED WITH ALCOHOL CONSUMPTION

(71) Applicant: Monir Elias, San Diego, CA (US)

(72) Inventor: Monir Elias, San Diego, CA (US)

(73) Assignee: Purple Biosciences LLC, San Diego, CA (US)

( * ) Notice: Subject to any disclaimer, the term of this patent is extended or adjusted under 35 U.S.C. 154(b) by 256 days.

(21) Appl. No.: 16/799,792

(22) Filed: Feb. 24, 2020

Related U.S. Application Data

(60) Provisional application No. 62/809,497, filed on Feb. 22, 2019.

(51) Int. Cl.
| | |
|---|---|
| *A61K 31/366* | (2006.01) |
| *A61K 31/198* | (2006.01) |
| *A61K 31/351* | (2006.01) |
| *A61K 36/906* | (2006.01) |
| *A23L 2/395* | (2006.01) |
| *A61K 36/67* | (2006.01) |
| *A61K 9/00* | (2006.01) |
| *A61K 45/06* | (2006.01) |

(52) U.S. Cl.
CPC ............ *A61K 31/366* (2013.01); *A23L 2/395* (2013.01); *A61K 31/198* (2013.01); *A61K 31/351* (2013.01); *A61K 36/67* (2013.01); *A61K 36/906* (2013.01); *A61K 9/0019* (2013.01); *A61K 9/0053* (2013.01); *A61K 45/06* (2013.01)

(58) Field of Classification Search
CPC .................................................. A61K 31/366
See application file for complete search history.

(56) References Cited

U.S. PATENT DOCUMENTS

| | | | |
|---|---|---|---|
| 2008/0075710 A1* | 3/2008 | Cornett | A61K 31/375 424/94.63 |
| 2015/0342923 A1* | 12/2015 | Powell | A61K 31/198 424/756 |

* cited by examiner

*Primary Examiner* — Rei Tsang Shiao
(74) *Attorney, Agent, or Firm* — Haley Guiliano LLP

(57) ABSTRACT

A composition for mitigating, treating, and/or preventing symptoms associated with veisalgia. In one embodiment the composition comprises one or more ingredients selected from the group consisting of: dihydromyricetin, N-acetyl cysteine, salicin, quercetin, bromelain, opuntia, potassium, sodium, magnesium, B-vitamins, vitamin C, taurine, caffeine, monk fruit, turmeric, curcumin, ginger root, and black pepper extract. A method for treating symptoms associated with veisalgia is also described. In one embodiment, the composition is administered in liquid or pill form.

20 Claims, 2 Drawing Sheets

| Ingredient | Exemplary Amounts |
|---|---|
| B Vitamins (including B1 (thiamine HCL), B2 (riboflavin), B6 (pyridoxine HCL), and B12) | approximately 0.05 mg to approximately 80 mg |
| Black Pepper Extract | approximately 10 mg to approximately 40 mg |
| Bromelain | approximately 50 mg to approximately 100 mg |
| Cactus Extract | approximately 1.5 mg to approximately 300 mg |
| Caffeine | approximately 30 mg to approximately 100 mg |
| Citric Acid | approximately 10 mg to approximately 2000 mg |
| Curcumin Extract | approximately 100 mg to approximately 250 mg |
| Dihydromyricetin ("DHM") | approximately 50 mg to approximately 1200 mg |
| Flavorings | approximately 0 mg to approximately 5000 mg |
| Ginger Root Extract | approximately 50 mg to approximately 250 mg |
| Hydroxypropyl-beta cyclodextrin (HPBCD) | approximately 3 g to approximately 10 g |
| Magnesium | approximately 5 mg to approximately 3000 mg |
| Malic Acid | approximately 10 mg to approximately 2000 mg |
| Manganese | approximately 0.1 mg to approximately 20 mg |
| Milk Thistle | approximately 5 mg to approximately 200 mg |
| Monk Fruit | approximately 50 mg to approximately 500 mg |
| N-acetyl Cysteine or N-acetyl L-Cysteine ("NAC") | approximately 5 mg to approximately 250 mg |
| Opuntia | approximately 100 mg to approximately 500 mg |
| Other natural extracts | approximately 0 mg to approximately 2000 mg |
| Potassium | approximately 15 mg to approximately 4000 mg |
| Potassium Sorbate | approximately 20 mg to approximately 2000 mg |
| Quercentin | approximately 200 mg to approximately 800 mg |
| Sodium | approximately 30 mg to approximately 7000 mg |
| Taurine | approximately 100 mg to approximately 500 mg |
| Turmeric Root Extract | approximately 500 mg to approximately 1500 mg |
| Vitamen C (calcium ascorbate | approximately 6 mg to approximately 600 mg |
| Vitamin C | approximately 30 mg to approximately 150 mg |
| Willow Bark (Salicin) | approximately 40 mg to approximately 1000 mg |
| Zinc | approximately 0.1 mg to approximately 20 mg |

FIG. 1

COMPOSITIONS FOR PREVENTION AND TREATMENT OF SYMPTOMS ASSOCIATED WITH ALCOHOL CONSUMPTION

CROSS-REFERENCE TO RELATED APPLICATION

The present application claims priority to U.S. Provisional Patent Application No. 62/809,497 filed on Feb. 22, 2019, entitled "COMPOSITIONS FOR PREVENTION AND TREATMENT OF SYMPTOMS ASSOCIATED WITH ALCOHOL CONSUMPTION," the entire disclosure of which is incorporated by reference herein.

BACKGROUND OF THE INVENTION

1. Field of Invention

The present invention relates to the pharmacological treatment of veisalgia and, specifically, compositions for prevention, mitigation, and treatment of symptoms associated with alcohol consumption.

2. Description of Related Art

For thousands of years, humans have been making and consuming alcohol and have also been, presumably, over-consuming alcohol for thousands of years. Some studies have found evidence of intentionally fermented beverages that existed as early as the Neolithic period, some 12,000 years ago. Today, purposeful production and consumption of alcoholic beverages is common and often reflects cultural and/or religious peculiarities as much as geographical and sociological environments.

While consuming alcohol can give a desirable euphoric effect, it can also give a consumer a number of negative physiological and/or psychological side effects. For example, a consumer may experience headache, drowsiness, concentration problems, dry mouth, dizziness, fatigue, gastrointestinal distress (e.g., vomiting), absence of hunger, depression, sweating, nausea, hyper-excitability, and anxiety, among other symptoms. These symptoms are medically referred to as "veisalgia" and commonly referred to as a "hangover." Hangovers are generally attributed to a combination of dehydration and toxicity from impurities found in alcohol (congeners). These symptoms may be particularly severe, especially after heavy consumption of alcohol.

Some aspects of alcohol's negative effect on the body start when alcohol is digested and broken down. When the body breaks down alcohol, acetaldehyde is created as a byproduct. Acetaldehyde can be 10 to 30 times more toxic to humans than alcohol itself. Once present, the body reacts to the acetaldehyde, causing immune system responses by the body trying to defend itself from the toxic byproduct. As a result, various parts of the body become inflamed, including the skin, liver, pancreas, eyes, etc. This inflammation hinders or prevents the body from absorbing liquid, thereby preventing the body from improving the alcohol-induced dehydration.

Although veisalgia is generally not life-threatening, it may be extremely unpleasant and prevents the afflicted from performing at a typical level. Some studies estimate that 25% of college students have experienced a hangover within the previous seven days and 29% reported losing classroom time due to a hangover. Other studies estimate that excessive drinking costs the United States economy around $220B annually — approximately $1.90 per drink consumed in the United States.

Consuming alcohol may also adversely affect one's sleeping patterns. Alcohol can enter the brain within minutes of consumption. Initially, alcohol causes the consumer to feel drowsy when intoxicated. Alcohol mimics gamma-aminobutyric acid ("GABA"), the major inhibitory neurotransmitter in the brain. When bound to GABA receptors on a neuron, alcohol allows either the influx of negative (or efflux of positive) ions, giving the cell a more negative charge. Thus, the neuron's ability to fire is diminished. Similarly, alcohol also inhibits the brain's major excitatory neurotransmitter, glutamate, by blocking its function through N-methyl-D-aspartate ("NMDA") receptors binding (and similar effects through inhibited acetylcholine and serotonin receptor bindings). After an evening of drinking, GABA dominates the first half of the night of sleep, allowing the drinker to fall into a deep sleep. However, once GABA is metabolized, much of it becomes glutamate. When glutamate is released in certain regions of the brain, such as the reticular activating system, which partially regulates sleep, wake, and arousal, the drinker's sleep pattern is disrupted. This causes the consumer to wake. This cycle is referred to as the "rebound effect."

Various forms of "hangover cures" are utilized throughout the drinking population. For example, nonsteroidal anti-inflammatory drugs ("NSAIDs") such as aspirin and ibuprofen are used. NSAIDs are generally effective at relieving headaches and muscle aches. However, NSAIDs also cause intestinal irritability while not addressing other hangover symptoms including certain inflammation caused by alcohol consumption that cannot be treated with nSAIDs Vitamins are also used to combat hangover symptoms. Alcohol depletes some water-soluble vitamins, especially B complex vitamins. However, vitamin supplementation after the onset of a hangover will have little to no effect on the hangover following acute alcohol consumption. Moreover, there is little to no evidence that vitamin supplements alone improve acute hangover symptoms.

The amino acid, N-acetylcysteine or N-Acetyl L-Cysteine ("NAC"), is used to boost the production of the antioxidant glutathione and support more efficient alcohol metabolism while reducing oxidative damage to the body. It has been studied as a protective agent, rather than a hangover treatment. The results of some animal studies suggest that NAC may decrease ethanol induced hypertension and acetaldehyde levels in rats, but there is little evidence to support NAC's efficacy as a treatment for hangovers in human subjects.

Some people also use caffeine to treat hangovers. Caffeine is a commonly used stimulant to combat the lethargy and headaches associated with hangovers. However, many caffeinated drinks such as coffee are diuretics and can exacerbate the dehydration associated with the hangover.

Another common hangover remedy is to drink more alcohol to ease the symptoms — sometimes referred to as "taking the hair of the dog" or "hair of the dog that bit you." The notion here is that hangovers are a form of alcohol withdrawal and drinking more alcohol will ease the withdrawal. However, this perpetuates the cycle of drinking, ultimately prolonging the hangover, and can lead to addiction.

One attempt to cure hangovers is U.S. Pat. No. 9,603,830 to Powell. However, this reference only discloses a treatment in a pill form and does not address many sources of symptoms associated with hangovers. For example, Powell does not attempt to redress the inflammation and allergic reactions associated with hangovers.

Another attempt to cure hangover is U.S. Pat. No. 6,485,758 to Mirza, et al. However, this reference does not address many sources of symptoms associated with hangovers. For example, like Powell, Mirza does not attempt to redress the inflammation or certain allergic reactions associated with hangovers.

A common problem to most currently available hangover remedies is that the antidotes are applied typically when the hangover symptoms have already commenced, i.e. the critical period to prevent and/or treat adverse symptoms have progressed too long to be efficacious. Further, most commercially-available hangover remedies fail to address inflammation effects of alcohol toxicity by specifically using anti-inflammatory agents. Typically, hangover symptoms peak when the blood alcohol content ("BAC") is near or at zero. Therefore, what is needed is a hangover treatment that contains compositions that mitigate symptoms associated with veisalgia and that enable the body to prevent a hangover from setting in. This need has heretofore remained unsatisfied.

SUMMARY OF THE INVENTION

The present invention overcomes these and other deficiencies of the prior art by providing a composition for veisalgia treatment that mitigates and prevents its symptoms.

In an embodiment of the invention, a composition stimulates enzymes associated with metabolizing alcohol and/or acetaldehyde—both toxic substances—into acetate—a non-toxic substance. In some embodiments, the composition is directed to stimulating alcohol dehydrogenases ("ADH") — a group of dehydrogenase enzymes that occur in many organisms and facilitate the interconversion between alcohols and aldehydes or ketones with the reduction of nicotinamide adenine dinucleotide ("NAD") to NADH. ADH serves to break down alcohols that otherwise are toxic, and they also participate in generation of useful aldehyde, ketone, or alcohol groups during biosynthesis of various metabolites.

In another embodiment, the present invention stimulates the body's production of aldehyde dehydrogenases ("ALDH")—a group of enzymes that catalyze the oxidation of aldehydes. ALDH converts aldehydes to carboxylic acids.

In an exemplary embodiment of the present invention, a composition for treating symptoms associated with veisalgia comprises dihydromyricetin, N-acetyl cysteine, and salicin. In some embodiments, the composition further comprises at least one of the ingredients selected from the group consisting of: quercetin, bromelain, opuntia, potassium, sodium, magnesium, B-vitamins, vitamin C, taurine, caffeine, turmeric, curcumin, milk thistle, monk fruit, hydroxypropyl-beta cyclodextrin, ginger root, and black pepper extract. In some embodiments, the composition is integrated into a liquid. In some embodiments, the composition is integrated into a capsule, tablet, chewable tablet, or pill. In some embodiments, the composition is a powder or liquid form and is readily integratable into food or drink.

In another exemplary embodiment of the present invention, a method for treating symptoms associated with veisalgia comprises administering, to a patient, a composition comprising dihydromyricetin, N-acetyl cysteine, and salicin. In some embodiments, the composition further comprises quercetin, bromelain, opuntia, potassium, sodium, magnesium, B-vitamins, vitamin C, taurine, caffeine, turmeric, curcumin, milk thistle, monk fruit, hydroxypropyl-beta cyclodextrin, ginger root, or black pepper extract, or a combination thereof In some embodiments, the composition is administered as a liquid. In some embodiments, the composition is administered as a capsule, tablet, chewable tablet, or pill. In some embodiments, the composition is administered via food or drink. In some embodiments, the composition is administered by injection intravenously, intramuscularly, intrathecally, or subcutaneously; sublingually or buccally; rectally or vaginally; placed in the eye by the ocular route or the ear by the otic route; nasally; inhalation or by nebulization; applied to the skin cutaneous for a local topical or body wide systemic effect; or delivered through the skin by patch transdermally for systemic effect.

The foregoing, and other features and advantages of the invention, will be apparent from the following, more particular description of the preferred embodiments of the invention, the accompanying drawings, and the claims.

BRIEF DESCRIPTION OF THE DRAWINGS

For a more complete understanding of the present invention, the objects and advantages thereof, reference is now made to the ensuing descriptions taken in connection with the accompanying drawings briefly described as follows:

FIG. 1 illustrates a table of exemplary amounts of ingredients, all various subsets of which are found in one or more embodiments of the present invention.

DETAILED DESCRIPTION OF PREFERRED EMBODIMENTS

Figure 2:
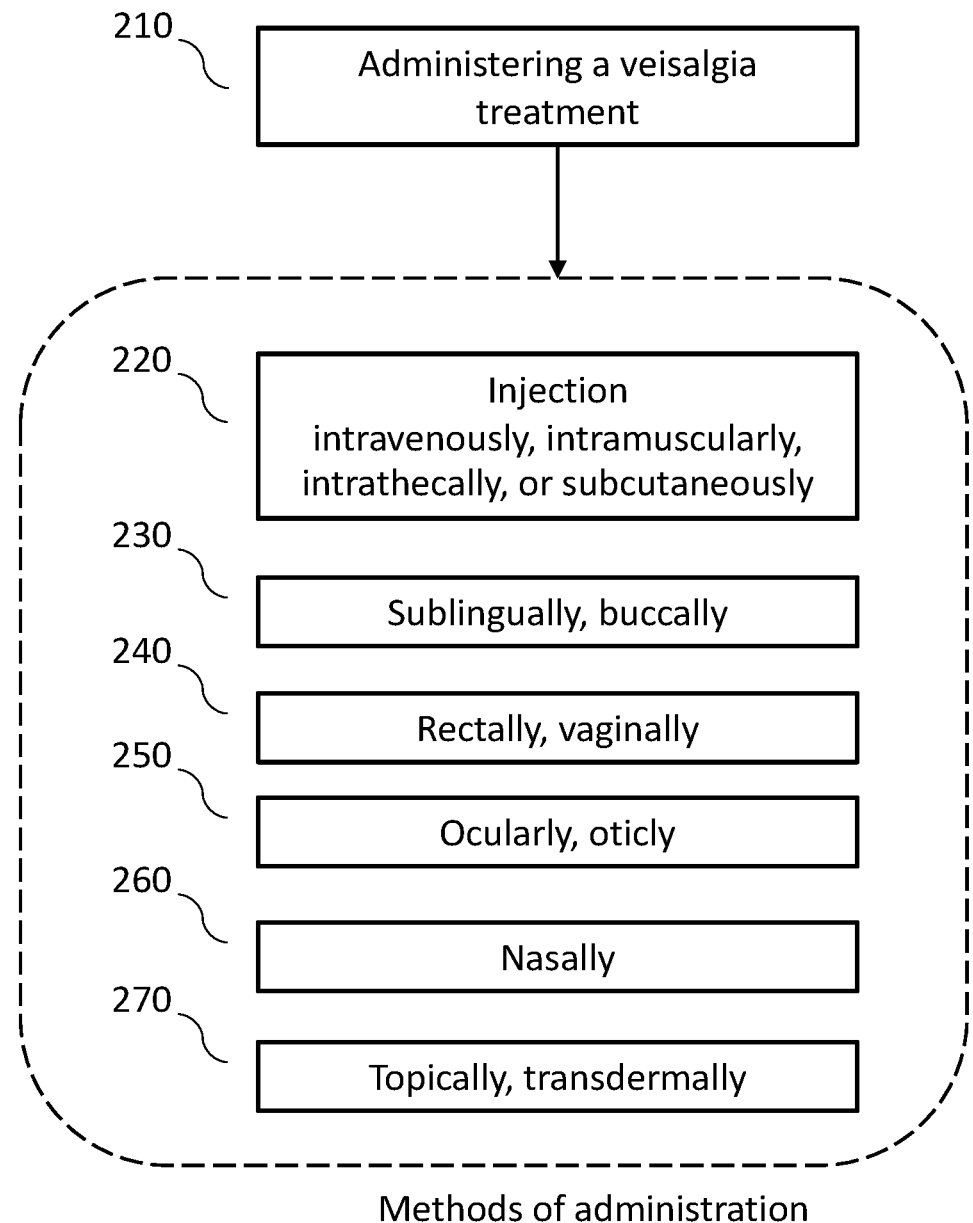
FIG. 2 illustrates exemplary methods of administering a composition for treating veisalgia.

Preferred embodiments of the present invention and their advantages may be understood by referring to FIGS. 1-2. Further features and advantages of the invention, as well as the structure and operation of various embodiments of the invention, are described in detail below. Although the invention is described in the context of a compound, any form may be implemented such as, but not limited to a powder, a pill, or a liquid, or other form suitable for various administrations, including as a nutritional supplement to treat other maladies such as headaches, dehydration, fatigue, and sensitivity to light and sound.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Moreover, the described features, structures, or characteristics of the invention may be combined in any suitable manner in one or more embodiments. It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents. Reference will now be made in detail to the preferred embodiments of the invention.

In an exemplary embodiment of the present invention and with reference to FIG. 1, a composition for veisalgia treatment comprises dihydromyricetin ("DHM"). DHM is used as an alcohol metabolism accelerator. DHM may be found naturally in the Japanese raisin tree (hovenia dulcis) and has been used in Chinese herbal tea. DHM may also be referred to as ampelopsin and found in vine tea extract. DHM accelerates alcohol metabolism but it can also prevent alcohol from affecting the brain's GABA receptors, thereby mitigating or preventing the rebound effect. The composition for veisalgia treatment may further comprise Salicin. Salicin is commonly found in Willow Bark and may be utilized in various concentrations. For example, some embodiments comprise Willow Bark having 15% to 98% concentration of salicin. Salicin is an alcoholic beta-glucoside and is produced in willow (salix) bark and has anti-inflammatory properties. Salicin is also commonly found in the bark of populus species, and the leaves of willows and poplars. It may also be found in castoreum, which may be used as an analgesic, anti-inflammatory, and antipyretic. The composition for veisalgia treatment may further comprise NAC.

In another exemplary embodiment of the present invention, a composition for veisalgia treatment may further comprise quercetin—a chemical found naturally in a number of foods and in some herbs. It acts as an antioxidant and also possesses anti-inflammatory and antihistamine properties, which reduces inflammation and allergic reactions triggered by alcohol. Other embodiments include bromelain, which supports normal mucosal tissue function and enhances the absorption of quercetin. Some embodiments include a combination of quercetin and bromelain, while other embodiments may include the combination of quercetin and bromelain in leu of salicin.

In another exemplary embodiment of the present invention, a composition for treating veisalgia mitigates adverse alcohol effects in the body by accelerating alcohol metabolism in the liver and supporting the immune system.

In another exemplary embodiment of the present invention, a composition for treating veisalgia functions as an alcohol metabolism accelerator and as a natural anti-inflammatory. The dual benefit contributes to positive effects on headache and fatigue post-alcohol overconsumption.

In another exemplary embodiment of the present invention, a composition for treating veisalgia comprises at least one anti-inflammatory agent that attenuates headaches or muscle aches associated with veisalgia.

In another exemplary embodiment of the present invention, the at least one anti-inflammatory agent is one selected form a group including: salicin (willow bark), Quercetin, Bromelain, or a combination thereof.

In another exemplary embodiment of the present invention, a composition for veisalgia treatment comprises an extract of Opuntia ficus-indica. Opuntia ficus-indica is commonly referred to as prickly pear and is a genus in the cactus family, Cactaceae. Various forms of Opuntia (or prickly pear) may be used. For example, some embodiments of the present invention comprise the extract Tex-OE® which includes special active molecules derived from the skin of the fruit of the Prickly Pear. Some embodiments include cactus extract at a concentration of 4:1.

In another exemplary embodiment of the present invention, a composition for veisalgia treatment comprises caffeine.

In another exemplary embodiment of the present invention, a composition for veisalgia treatment comprises turmeric. Some embodiments comprise turmeric root extract. Other embodiments comprise curcumin extract. Curcumin is a natural anti-inflammatory and many of the adverse effects of alcohol hangovers are due to inflammation. In an exemplary embodiment of the invention, a composition for veisalgia treatment comprises approximately 200 mg to 1000 mg of curcumin and/or turmeric. Some embodiments include turmeric comprising approximately 10% curcumin.

In another exemplary embodiment, a composition for veisalgia treatment comprises Monk Fruit, which has anti-inflammatory properties and is safe for diabetes in that there are no calories, carbs, sugar, or fat. In an exemplary embodiment of the invention, a composition for veisalgia treatment comprises approximately 5 mg to 200 mg of Monk Fruit. Some embodiments include Monk Fruit MV 50%.

In another exemplary embodiment of the present invention, a composition for veisalgia treatment comprises Milk Thistle, which supports liver health. In an exemplary embodiment of the invention, a composition for veisalgia treatment comprises approximately 5 mg to 200 mg of Milk Thistle. Some embodiments include Milk Thistle comprising approximately 80% silymarin.

In another exemplary embodiment of the present invention, a composition for veisalgia treatment comprises hydroxypropyl-beta cyclodextrin ("HPBCD"), a highly soluble substance which can be used to increase the solubility of the ingredients. HPBCD may be used, for example, in integrating the composition for veisalgia treatment into a liquid form. Additionally, HPBCD may be used to enhance the absorption rate of the composition for treating veisalgia. In an exemplary embodiment of the invention, a composition for veisalgia treatment comprises approximately 3 g to 8 g of HPBCD.

In another exemplary embodiment of the present invention, a composition for veisalgia treatment comprises ginger. Some embodiments comprise ginger root extract while others comprise powdered ginger.

In another exemplary embodiment of the present invention, a composition for veisalgia treatment comprises taurine. Other embodiments comprise black pepper extract.

In another exemplary embodiment, a composition for veisalgia treatment comprises potassium, sodium, and/or magnesium, either individually or in combination. Alcohol, like any diuretic, depletes the body of potassium and salts. In such and embodiment, these minerals in this composition is necessary for body rehydration and proper nerve and muscle functions. Moreover, magnesium may support the alcohol dehydrogenase ("ADH"), an enzyme in accelerating the alcohol break down and eliminating it from the body. Some embodiments include magnesium comprising approximately 60% oxide.

In another exemplary embodiment, a composition for veisalgia treatment comprises various B vitamins, including but not limited to, thiamine (B1), riboflavin (B2), niacin (B3), pantothenic acid (B5), biotin (B7), folic acid, vitamin B6, and/or vitamin B12. Some embodiments comprise thiamine HCL, riboflavin 5-phosphate, and/or pyridoxine HCL.

In another exemplary embodiment, a composition for veisalgia treatment comprises vitamin C. Some embodiments include vitamin C comprising calcium ascorbate.

In another exemplary embodiment of the present invention, a composition for veisalgia treatment is a compound comprising a combination of DHM, willow bark (salicin), N-acetyl cysteine ("NAC"), opuntia (nopal cactus), quercetin, and/or bromelain.

In another exemplary embodiment of the present invention, a composition for veisalgia treatment is a beverage comprising DHM, willow bark, NAC, opuntia, a combination of B vitamins, potassium, sodium, magnesium, quercetin, and/or bromelain.

The table depicted in FIG. 1 illustrates some of the ingredients of the present invention, along with exemplary amounts for each. Notably, the table is not offered as an exhaustive or exclusive list but rather as exemplary ingredients. Moreover, the ingredients may be used by themselves, in combination with some or all of the other ingredients listed, or with other ingredients not listed, without departing from the embodiments contemplated herein. Further, the ingredients listed may be incorporated in various concentrations. For example, willow bark includes salicin in varying concentrations. Willow bark may have salicin concentrations of anywhere between approximately 15% to approximately 98% -the entire range of which may be used in amount varying between approximately 40 mg to approximately 180 mg. Additionally, the ingredients listed may be utilized in treatments for veisalgia outside of the amounts shown without departing from the embodiments contemplated herein. In addition to the exemplary ingredients disclosed, other ingredients may be used to assist administration. In one embodiment, HPBCD is used to make a homogenous liquid by improving the water solubility of the ingredients. For example, in an embodiment where the veisalgia treatment is integrated into a drinkable liquid, the veisalgia treatment may further include natural and/or artificial flavorings or colors. In one embodiment, the natural flavorings include monk fruit. In another example where the veisalgia treatment is integrated into a capsule or tablet, the veisalgia treatment may also include binding agents or other inactive ingredients.

In another exemplary embodiment of the present invention and with reference to FIG. 2, a composition for veisalgia treatment 200 may be administered in a variety of ways at step 210. The veisalgia treatment 200 comprises composition according to the embodiments described above. The veisalgia treatment 200 may be administered by injection including intravenously, intramuscularly, intrathecally, or subcutaneously. In another embodiment, as shown at step 230, the veisalgia treatment 200 may be administered sublingually or buccally. In another embodiment, as shown at step 240, the veisalgia treatment 200 may be administered rectally or vaginally. In another embodiment, as shown at step 250, the veisalgia treatment 200 may be administered ocularly (through the eye) or oticly (through the ear). In another embodiment, as shown at step 260, the veisalgia treatment 200 may be administered nasally by, for example, through inhalation or by nebulization. In another embodiment, as shown at step 270, the veisalgia treatment 200 may be administered topically or transdermally, for example by patch.

Although the present invention may discuss a composition for veisalgia treatment in the form of a compound, other forms may be utilized without departing from the embodiments contemplated herein. For example, the present invention may be administered orally. In such an embodiment, the veisalgia treatment may be integrated into a liquid, capsule, tablet, chewable tablet, or pill. In such an embodiment, a liquid veisalgia treatment may be prepared by first combining HPBCD, DHM, Salicin, NAC, and Turmeric (as exemplary ingredients). Next, the remaining ingredients (such as flavoring compounds), if any, may be separately combined. The two mixtures may then be combined to finalize the liquid veisalgia treatment.

Some embodiments further include flavorings. For example, various embodiments comprise natural flavorings including lemon and lime flavorings. Other embodiments may include citric acid and/or malic acid.

In other embodiments, a composition for veisalgia treatment may be integrated into food by, for example, being included in the food's preparation, e.g., added as an ingredient into a food such as candy/protein/power bar or mixed in yogurt, or may be integrated into food in the way many condiments are, e.g., a powder or liquid form that is sprinkled on or added into food much like salt, pepper, ketchup, or mustard. In other embodiments, the veisalgia treatment may be integrated into the drinker's alcoholic beverage, either being mixed into the alcohol itself or added by the consumer/preparer of the beverage. An advantage to this embodiment is the drinker may ensure the veisalgia treatment is indeed administered and/or administered in the proper amount.

The present invention may also be administered to a patient in other ways without departing from the embodiments contemplated herein including: given by injection into a vein (intravenously, IV), into a muscle (intramuscularly, IM), into the space around the spinal cord (intrathecally), or beneath the skin (subcutaneously, SC); placed under the tongue (sublingually) or between the gums and cheek (buccally); inserted in the rectum (rectally) or vagina (vaginally); placed in the eye (by the ocular route) or the ear (by the otic route); sprayed into the nose and absorbed through the nasal membranes (nasally); breathed into the lungs, usually through the mouth (by inhalation) or mouth and nose (by nebulization); applied to the skin (cutaneously) for a local (topical) or bodywide (systemic) effect; and/or delivered through the skin by patch (transdermally) for systemic effect.

Although the present invention is described herein as a composition for treating veisalgia, the invention may be used to treat other maladies, including, for example, dehydration, nausea, fatigue, headache, light and sound sensitivity, and dizziness. The present invention may also be used to treat patients with migraine headaches. Migraine patients reported that the presently described veisalgia treatment helped them (on more than one occasion) to cope with alcohol-triggered migraines. After taking the presently described veisalgia treatment, patients reported a "surprisingly positive" experience of waking up with no migraine or headache triggered by alcohol overconsumption. Additionally, although the present invention is shown and described as comprising various specific ingredients, the present invention may include all subsets of disclosed ingredients, without departing from the embodiments contemplated herein.

The composition for treatment of veisalgia may be administered in capsule form. In such an embodiment, the ingredients are mixed together until homogenous. Various types of encapsulation may be utilized, for example, single-piece gel encapsulation (soft capsules) and two-piece gel encapsulation (hard capsules). The ingredients may be suspended in a liquid (such as oil) and placed inside of the capsule. Alternatively, the composition for treatment of veisalgia may be offered in liquid form. In such an embodiment, the specified ingredients may be homogenously mixed together and dissolved in a medium.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed herein, but instead as being fully commensurate in scope with the following claims.

I claim:

1. A composition comprising between 10% and 69% by weight of dihydromyricetin, and between 1% and 35% by weight of salicin.

2. The composition of claim 1 further comprising at least one of the ingredients selected from the group consisting of: bromelain, potassium, sodium, magnesium, B-vitamins, vitamin C, caffeine, milk thistle, hydroxypropyl-beta cyclodextrin, N-acetyl cysteine, and ginger root; and at least one ingredient selected from the group consisting of quercetin, opuntia, taurine, turmeric, curcumin, monk fruit, and black pepper extract.

3. The composition of claim 1, wherein the composition is integrated into a liquid.

4. The composition of claim 1, wherein the composition is integrated into a capsule, tablet, chewable tablet, or pill.

5. The composition of claim 1, wherein the composition is in powder or liquid form and is readily integratable into food or drink.

6. A method for treating symptoms associated with veisalgia comprising: administering, to a patient, a composition comprising between 5% and 69% by weight of dihydromyricetin, and between 1% and 39% by weight of salicin.

7. The method of claim 6, wherein the composition further comprises bromelain, potassium, sodium, magnesium, B-vitamins, vitamin C, caffeine, milk thistle, hydroxypropyl-beta cyclodextrin, N-acetyl cysteine, or ginger root, or a combination thereof; and at least one ingredient selected from the group consisting of quercetin, opuntia, taurine, turmeric, curcumin, monk fruit, and black pepper extract.

8. The method of claim 6, wherein the composition is integrated into a liquid.

9. The method of claim 6, wherein the composition is integrated into a capsule, tablet, chewable tablet, or pill.

10. The method of claim 6, wherein the composition is administered via food or drink.

11. The method of claim 6, wherein the composition is administered by injection intravenously, intramuscularly, intrathecally, or subcutaneously; sublingually or buccally; rectally or vaginally; placed in the eye by the ocular route or the ear by the otic route; nasally; inhalation or by nebulization; applied to the skin cutaneous for a local topical or body wide systemic effect; or delivered through the skin by patch transdermally.

12. The composition of claim 1 further comprising between 10% and 40% by weight of hydroxypropyl-beta cyclodextrin.

13. The composition of claim 1 further comprising between 30% and 69% by weight of dihydromyricetin, between 10% and 35% by weight of salicin, and between 5% and 15% by weight of milk thistle.

14. The composition of claim 1 further comprising between 30% and 69% by weight of dihydromyricetin, between 10% and 35% by weight of salicin, and between 5% and 15% by weight of opuntia.

15. The composition of claim 1 further comprising between 30% and 69% by weight of dihydromyricetin, between 10% and 35% by weight of salicin, between 1% and 10% by weight of milk thistle, and between 1% and 10% by weight of quercetin.

16. The method of claim 6, wherein the composition further comprises between 30% and 69% by weight of dihydromyricetin, between 10% and 35% by weight of salicin, between 1% and 10% by weight of opuntia, between 1% and 10% by weight of milk thistle, and between 1% and 10% by weight of quercetin.

17. The method of claim 6, wherein the composition further comprises between 30% and 69% by weight of dihydromyricetin, between 10% and 35% by weight of salicin, and between 5% and 15% by weight of milk thistle.

18. The method of claim 6, wherein the composition further comprises between 30% and 69% by weight of dihydromyricetin, between 10% and 35% by weight of salicin, and between 5% and 15% by weight of opuntia.

19. The method of claim 6, wherein the composition further comprises between 10% and 29% by weight of dihydromyricetin, between 10% and 29% by weight of salicin, between 1% and 10% by weight of opuntia, between 1% and 10% of milk thistle, and between 1% and 10% by weight of quercetin.

20. The method of claim 6, wherein the composition further comprises between 5% and 39% by weight of dihydromyricetin, between 5% and 39% by weight of salicin, between 1% and 10% by weight of opuntia, between 1% and 10% by weight of milk thistle, and between 1% and 10% by weight of quercetin.

* * * * *